(12) United States Patent
Chitre et al.

(10) Patent No.: US 7,826,905 B2
(45) Date of Patent: *Nov. 2, 2010

(54) SELF-SEALING INSULATION EMPLOYED ON A CATHETER OR LEAD

(75) Inventors: Yougandh Chitre, Valencia, CA (US); Cheuk Tang, Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 362 days.

This patent is subject to a terminal disclaimer.

(21) Appl. No.: 11/946,486

(22) Filed: Nov. 28, 2007

(65) Prior Publication Data
US 2008/0077216 A1 Mar. 27, 2008

Related U.S. Application Data

(63) Continuation of application No. 11/206,448, filed on Aug. 17, 2005, now Pat. No. 7,353,066.

(51) Int. Cl.
*A61N 1/05* (2006.01)
(52) U.S. Cl. .................. 607/116; 607/119; 600/373
(58) Field of Classification Search ............... 607/116, 607/119, 122, 125; 600/372, 373, 374, 375, 600/377; 336/94, 96
See application file for complete search history.

(56) References Cited

U.S. PATENT DOCUMENTS

| | | | |
|---|---|---|---|
| 3,896,969 A | 7/1975 | Basile | |
| 4,228,839 A | 10/1980 | Bohm et al. | |
| 4,577,642 A | 3/1986 | Stokes | |
| 5,133,742 A | 7/1992 | Pinchuk | |
| 5,231,996 A | 8/1993 | Bardy et al. | |
| 5,466,252 A | 11/1995 | Soukup et al. | |
| 5,628,774 A | 5/1997 | Helland et al. | |
| 5,755,762 A | 5/1998 | Bush | |
| 5,843,149 A | 12/1998 | Ebert et al. | |
| 5,902,329 A | 5/1999 | Hoffmann et al. | |
| 6,508,898 B1 | 1/2003 | Rustad et al. | |
| 6,701,191 B2 | 3/2004 | Schell | |
| 6,990,378 B1 | 1/2006 | Algee | |

OTHER PUBLICATIONS

Levy, M.C. et al., "Fourier transform infrared spectroscopic studies of human serum albumin microcapsules prepared by interfacial cross-linking with terephthaloylchloride: Influence of polycondensation pH on spectra and relation with microcapsule morphology and size," J Pharm Sci Jun. 1991;80(6):578-585.

(Continued)

*Primary Examiner*—Scott M Getzow
*Assistant Examiner*—Joseph M Dietrich

(57) ABSTRACT

An implantable electrical medical lead for a pulse generator includes a distal electrode, a connector for electrical connection with the pulse generator, an electrical conductor within the lead extending between the connector and the distal electrode, and an insulating sheath of flexible resilient material normally covering the electrical conductor having self sealing properties to re-insulate the electrical conductor in the event a rupture of the sheath should occur which exposes the electrical conductor. The insulating sheath is of polymeric material embedded with a plurality of pellets, each pellet having a frangible shell containing a liquid sealing material that solidifies when the frangible shell is broken and thereby filling in any voids in the polymeric material.

9 Claims, 3 Drawing Sheets

OTHER PUBLICATIONS

NonFinal Office Action, mailed Jul. 20, 2007: U.S. Appl. No. 11/206,448.

Notice of Allowance, mailed Nov. 9, 2007: U.S. Appl. No. 11/206,448.

NonFinal Office Action, mailed Jan. 25, 2010—U.S. Appl. No. 11/946,453.

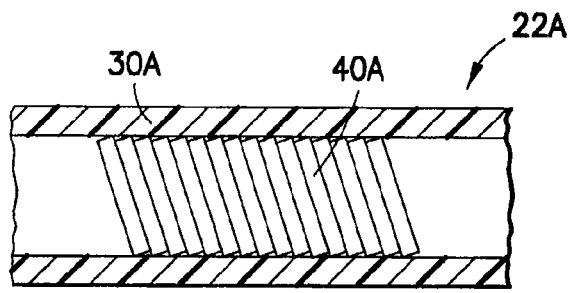
FIG.2
PRIOR ART
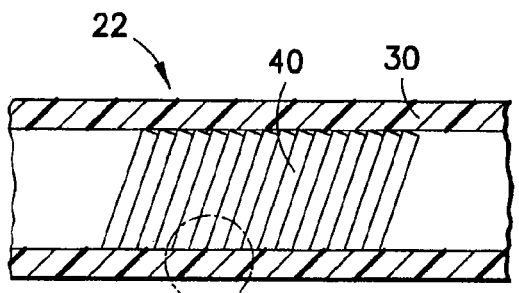
FIG.3
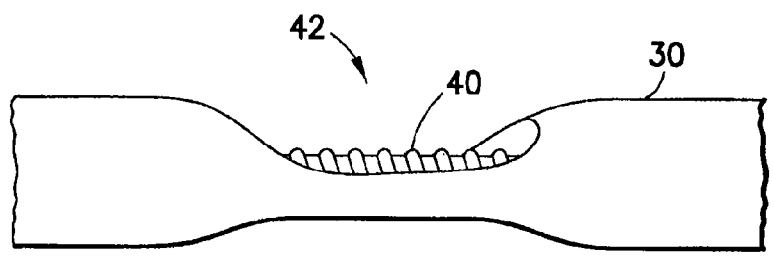
FIG.4
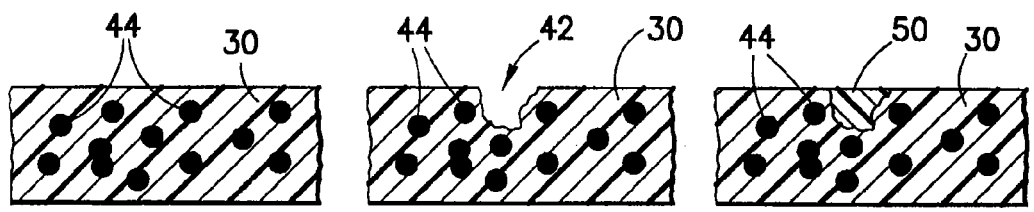
FIG.5A   FIG.5B   FIG.5C

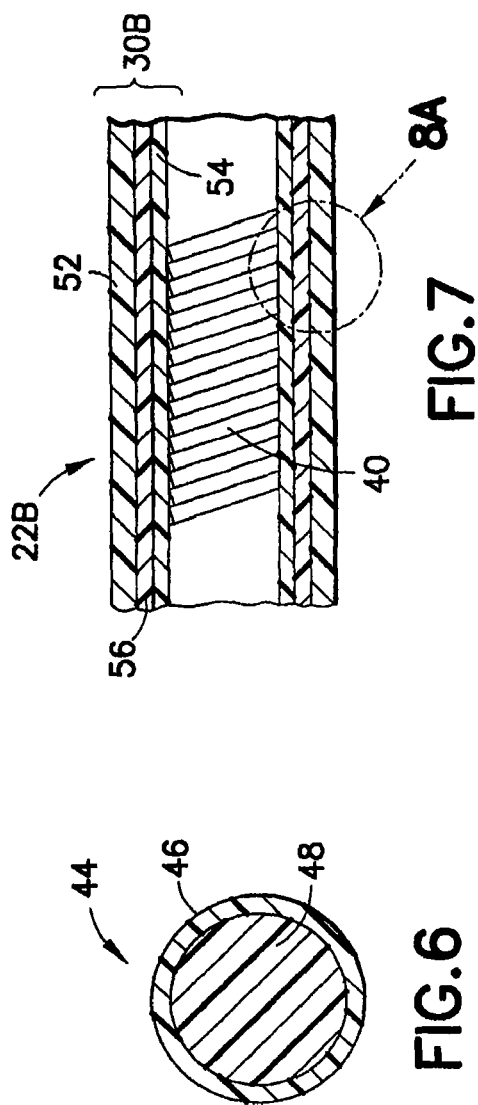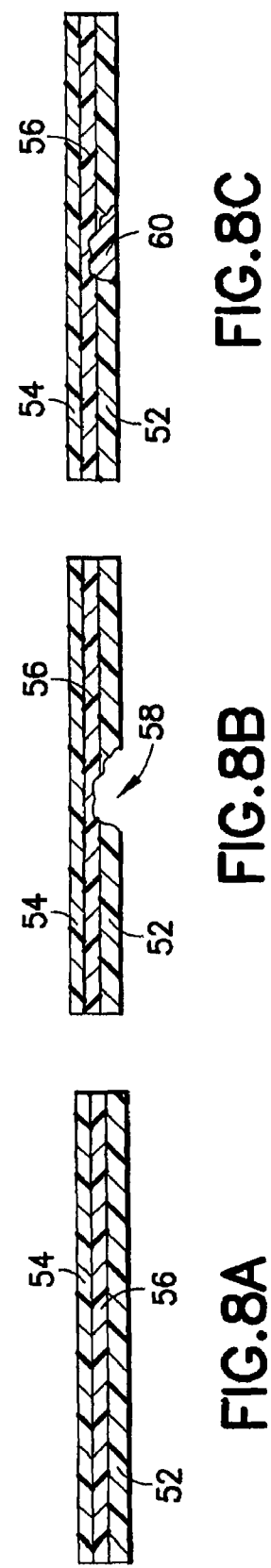

SELF-SEALING INSULATION EMPLOYED ON A CATHETER OR LEAD

CROSS-REFERENCE TO RELATED APPLICATIONS

This is a continuation of copending U.S. patent application Ser. No. 11/206,448, filed Aug. 17, 2005, titled "Self-Sealing Insulation Employed on a Catheter or Lead."

FIELD OF THE INVENTION

The present invention relates generally to implantable cardiac stimulation leads and, more particularly, to such leads providing a self-sealing insulation mechanism to mitigate the deleterious effects of abrasion.

BACKGROUND OF THE INVENTION

Historically, the material of choice for insulations employed on pacing/defibrillation leads has been silicone due to its superior handling characteristics as compared to its polyurethane material counterpart. The drawback however, is the compromised abrasion resistance that the silicones exhibit. A breach in the outer insulation employed on leads has been extensively reported in the literature and is an especially potentially serious failure mode of Implantable Cardioverter Defibrillation (ICD) systems. This failure mode can result in the inhibition of the delivery of high voltage therapy due to a direct arc from the lead to the can if the insulation breach exposes one of the defibrillation conductors. The failure mode can also manifest itself in the form the delivery of inappropriate therapy due to the detection of noise if the breach exposes any of the sensing or pacing conductors of the lead.

The problem is further compounded by the increasing number of leads that are implanted in patients and their subsequent interaction resulting in abrasion.

Known techniques, materials, and constructions which preceded the present invention include:

- a soft polyurethane composition having a low level of an aromatic phosphate or phosphonate plasticizer that will perform well as a self-sealing liner to flat-proof pneumatic tires, and will withstand the high temperatures of the tire retread process and still be functional;
- an implantable lead having a helically wound conductor with a surrounding tubular insulating layer of elastomeric material such as silicone or polyurethane and an additional coaxial tubular exterior biocompatible layer of porous PTFE having a microstructure of nodes interconnected by fibrils, the exterior tubular layer of porous PTFE fitted coaxially over the elastomeric tubular layer whereby the porous PTFE tubular layer is in longitudinal compression and the fibrils within the microstructure have a bent and wavy appearance and such that any portion of the length of the porous PTFE tubing in longitudinal compression allows that portion of the length of the lead wire to be extensible to a controlled extent limited by the straightening of the bent fibrils within the porous PTFE microstructure;
- a lead exhibiting improved combined biodegradation, blood surface compatibility, wear and flexibility characteristics including an outer or first insulation of silicone encircling the conductor and a second insulation of polyurethane encircling the silicone rubber insulation;
- a continuous sheath of open-celled porous plastic, preferably ePTFE, is used on the outside of an implantable lead, such that when the pores of the sheath are filled with saline, the lead can deliver defibrillation energy through the pores in the plastic, pore size being chosen to discourage tissue ingrowth while allowing for delivery through it of defibrillation energy.
- an extractable lead contains a hydrogel coating having a thickness increase greater than 10% when hydrated, the thick coating used to provide a shear layer so that the coating tears during extraction, either at the coating/lead interface, between layers of the coating itself, or at the coating/tissue interface.

None of the foregoing instances disclose or suggest the present invention and it was in light of the foregoing that the present invention was conceived and has now been reduced to practice.

SUMMARY

An implantable electrical medical lead for a pulse generator includes a distal electrode, a connector for electrical connection with the pulse generator, an electrical conductor within the lead extending between the connector and the distal electrode, and an insulating sheath of flexible resilient material normally covering the electrical conductor. The insulating sheath has self sealing properties to re-insulate the electrical conductor in the event a rupture of the sheath should occur which exposes the electrical conductor. In one instance, the insulating sheath is of polymeric material embedded with a plurality of pellets, each pellet having a frangible shell containing a liquid sealing material that solidifies when the frangible shell is broken. In another instance, the insulating sheath includes an outer insulative layer, an inner insulative layer, and an intermediate plasticized layer to seal any occurring rupture in the insulating sheath and re-insulate the electrical conductor which has been exposed.

The invention teaches the concept and specific designs of insulations employed on catheters or leads that provide a self-sealing mechanism. Two different approaches are considered for providing a self-sealing insulation mechanism to mitigate the deleterious effects of abrasion. A first concept teaches the use of an insulation material extruded with appropriately dimensioned epoxy balls or pellets. In this instance, the self-sealing mechanism is brought about as follows: (1) when insulation material is subjected to conditions that result in the abrading away of the insulation of the lead or catheter, (2) underlying epoxy balls or pellets are impinged upon, (3) with the result that the epoxy balls are thereby broken and resulting in the flow of epoxy into areas of deficient insulation material, (4) such that voids in the insulation are sealed with the epoxy.

A second concept teaches the use of an inner layer (soft polyurethane or equivalent material) which includes among other things a plasticizer. A liner of PTFE, or equivalent material, can also be employed to protect the soft polyurethane layer from the conductor. When the liner is exposed due to abrasion of the outer insulation, the plasticized material flows and serves to seal the compromised voids in the insulation.

A primary feature of the invention is to provide an implantable cardiac stimulation lead with a self-sealing insulation mechanism to mitigate the deleterious effects of abrasion.

Another feature of the invention is to provide an insulating sheath of flexible resilient material normally covering the electrical conductor and extending from the proximal end to the distal end and having self sealing properties to re-insulate the electrical conductor in the event a rupture of the sheath should occur which exposes the electrical conductor.

Still another feature of the invention is to provide such a lead with an insulating sheath composed of polymeric material embedded with a plurality of pellets, each pellet having a frangible shell containing a liquid sealing material that fills the rupture and solidifies when the frangible shell is broken.

Yet a further feature of the invention is to provide such a lead with an insulating sheath which includes an outer insulative layer, an inner insulative layer, and a plasticized layer intermediate the outer insulative layer and the inner insulative layer to seal any occurring rupture in the insulating sheath and re-insulate the electrical conductor which has been exposed.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 2 is a detail cross section view of a known implantable lead;

FIG. 3 is a detail cross section view, similar to FIG. 2, of one embodiment of implantable lead in accordance with the invention;

FIG. 4 is a perspective view of a portion of the lead illustrated in FIGS. 1 and 3 depicting a rupture of the type to be repaired by the invention;

FIG. 5A is an enlarged cross section view of a portion of the lead illustrated in FIG. 3;

FIGS. 5B and 5C are enlarged cross section views, similar to FIG. 5A, illustrating subsequent events in the life of the lead in accordance with the invention;

FIG. 6 is a cross section view of a pellet of the kind shown, most clearly, embedded in the sheath in FIGS. 5A, 5B, and 5C;

FIG. 7 is a detail cross section view, similar to FIG. 3, of another embodiment of implantable lead in accordance with the invention;

FIG. 8A is an enlarged cross section view of a portion of the lead illustrated in FIG. 7; and FIGS. 8B and 8C are enlarged cross section views, similar to FIG. 8A, illustrating subsequent events in the life of the lead in accordance with the invention.

DETAILED DESCRIPTION OF THE PREFERRED EMBODIMENT

Figure 1:
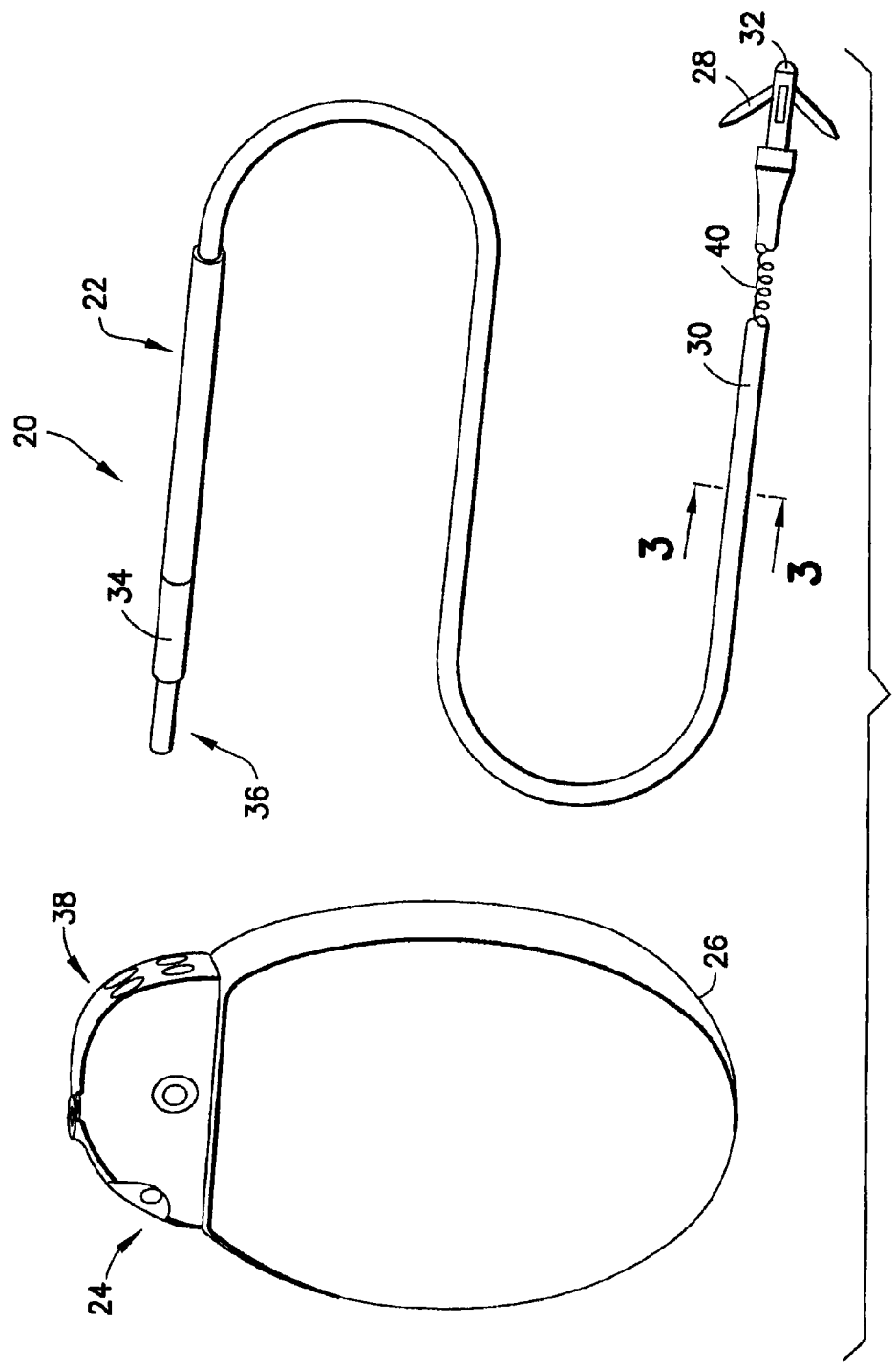
FIG. 1 is a perspective view illustrating a system embodying the invention including an implantable lead in combination with a stimulating medical device or pulse generator such as a pacemaker.

Refer now to the drawings and, initially, to FIG. 1 which illustrates a diagrammatic perspective view of a system 20 for coupling a body implantable medical electrical lead 22 to a medical device or pulse generator 24 including a sealed housing or casing 26 containing electronic circuitry for delivering electrical stimuli to body tissue. The lead 22 is illustrated to be of the endocardial type which may be attached to an interior wall of a heart by means of fixing tines 28, for example, which engage the tissue or trabeculae of the heart. Alternatively, the lead may be of the epicardial or myocardial type for which the present invention would also provide a significant benefit. The lead 22 also includes an insulating sheath 30 of flexible resilient polymeric material interconnecting a distal electrode 32 secured adjacent the interior wall of the heart, for example, and an electrical connector 34 at a proximal end 36 for attachment to the medical device or pulse generator 24, such as a pacemaker. The terms medical device, pulse generator, and pacemaker may be used interchangeably in this disclosure. Attachment of the electrical connector 34 to the pulse generator 24 is achieved via a connector assembly or header 38. Although the present invention will be described with reference to the embodiments shown in the drawings, it should be understood that the present invention can be embodied in many alternate forms or embodiments. In addition, any suitable size, shape or type of elements or materials could be used.

For purposes of comparison, FIG. 2 illustrates a construction of a known lead 22A with an electrical conductor 40A and overlying insulating sheath 30A which may have the foregoing characteristics.

In contrast, in accordance with the invention, the insulating sheath 30 (FIGS. 1 and 3) of the lead 22 is typically formed, by extrusion or in any other suitable manner, of silicone or polyurethane, or a combination of those materials. However, the invention is not limited to the use of these materials for fabrication of the insulating sheath. In a known construction, the insulating sheath 30 covers an electrical conductor 40 which extends between the proximal end 36 for attachment with the connector 34 and a distal end for attachment to the distal electrode 32. The insulating sheath 30 extends between the proximal and distal ends of the lead 22 and has self sealing properties to re-insulate the electrical conductor 40 in the event a rupture 42 (see FIG. 4) of the sheath should occur which exposes the electrical conductor.

The self sealing properties attributed to the insulating sheath 30 most clearly depicted in FIGS. 3, 5A, 5B, and 5C result from the presence of a plurality of pellets 44 embedded in the polymeric material of the sheath. Viewing FIG. 6, each pellet 44 has a frangible shell 46 containing a liquid sealing material 48 that serves to fill the rupture 42 (FIGS. 4, 5B) and solidifies as indicated by filler material 50 (FIG. 5C) when the frangible shell is broken. In order to assure an adequate supply of the liquid sealing material 48 to fill the rupture 42 and fully re-insulate the electrical conductor 40, it is necessary that the plurality of the pellets 44 occupy in the range of about 30% to about 70% of the volume of the insulating sheath 30. If the pellets 44 occupy less than about 30% of the volume of the insulating sheath 30, there will be an insufficient amount of the liquid sealing material 48 to adequately re-insulate the electrical conductor 40.

The desired result is achieved by the lead 22 when the insulating sheath 30 has a thickness in the range of about 0.003 inches to about 0.010 inches and when each of the pellets 44 has a transverse dimension in the range of about 0.0005 inches to about 0.0010 inches. Additionally, preferred materials for the shell 46 of the pellets 44 are polycarbonate and polyvinyl chloride and for the liquid sealing material 48 in each pellet is a body curable adhesive, preferably of the family of silicone adhesives. Again, while these materials well serve the purpose of the invention, other unnamed materials could also be useful.

In another instance, as seen in FIGS. 7, 8A, 8B, and 8C, an insulating sheath 30B for a lead 22B includes an outer insulative layer 52, an inner insulative layer 54, and a plasticized layer 56 intermediate the outer insulative layer and the inner insulative layer to seal any occurring rupture 58 in the insulating sheath and to re-insulate the electrical conductor 40 which has thereby been exposed. In this instance, when the plasticized layer 56 is exposed in the manner depicted in FIG. 8B, the plasticized material is thereby freed to flow into the rupture 58 and fill it with filler material 60 in the manner depicted in FIG. 8C.

For purposes of the invention, the outer insulative layer 52 of the insulating sheath is preferably composed of silicone, polyurethane, or a combination of those materials; the inner insulative layer 54 is preferably composed of a fluorinated polymer such as PTFE, silicone, polyurethane, or a combination of those materials, and the plasticized layer is preferably composed of a chemically softened silicone, polyurethane, or combination thereof. Once again, while these materials well serve the purpose of the invention, other unnamed materials could also be useful.

Additionally, dimension-wise, the outer insulative layer 52 has a thickness in the range of about 0.003 inches to about 0.010 inches, the inner insulative layer 54 has a thickness in the range of about 0.001 inches to about 0.005 inches, and the plasticizer layer 56 has a thickness in the range of about 0.0005 inches to about 0.0050 inches.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable electrical medical lead extending between proximal and distal ends for use with a pulse generator to be implanted within a human body, the lead comprising:
   a distal electrode;
   a connector providing an electrical connection with the pulse generator;
   an electrical conductor within the lead extending between a proximal end for attachment with the connector and a distal end for attachment to the distal electrode; and
   an insulating sheath of flexible resilient material normally covering the electrical conductor and extending from the proximal end to the distal end and having self sealing properties to re-insulate the electrical conductor in the event of an abrasion of the sheath;
   wherein the insulating sheath is of polymeric material embedded with a plurality of pellets, each pellet having a frangible shell containing a liquid sealing material that fills the rupture and solidifies when the frangible shell is broken;
   wherein the flexible resilient material of the insulating sheath is selected from the group consisting of silicone or polyurethane or a combination thereof; and
   wherein the liquid sealing material in each pellet is a body temperature curable adhesive.

2. An implantable electrical medical lead as set forth in claim 1
   wherein the plurality of the pellets occupy in the range of about 30% to about 70% of the volume of the insulating sheath.

3. An implantable electrical medical lead as set forth in claim 1
   wherein the insulating sheath has a thickness in the range of about 0.003 inches to about 0.010 inches; and
   wherein each of the pellets has a transverse dimension in the range of about 0.0005 inches to about 0.0010 inches.

4. An implantable electrical medical lead as set forth in claim 1
   wherein the plurality of the pellets occupy in the range of about 30% to about 70% of the volume of the insulating sheath;
   wherein the insulating sheath has a thickness in the range of about 0.003 inches to about 0.010 inches; and
   wherein each of the pellets has a transverse dimension in the range of about 0.0005 inches to about 0.0010 inches.

5. A method of sealing an implantable electrical medical lead, the integrity of which may be compromised, the lead extending between a proximal end for attachment with a connector for providing an electrical connection with a pulse generator and a distal end for attachment to a distal electrode, the method comprising:
   (a) with an insulating sheath of flexible resilient material, covering the electrical conductor extending from the proximal end to the distal end;
   (b) providing the insulating sheath with self sealing properties to re-insulate the electrical conductor in the event a rupture of the sheath should occur which exposes the electrical conductor; the insulation sheath being a polymeric material; and
   (c) embedding the polymeric material of the insulating sheath with a plurality of pellets, each pellet having a frangible shell containing a liquid sealing material that fills the rupture and solidifies when the frangible shell is broken
   wherein the flexible resilient material of the insulating sheath is selected from the group consisting of silicone or polyurethane or a combination thereof; and
   wherein the liquid sealing material in each pellet is epoxy.

6. The method as set forth in claim 5
   wherein the plurality of the pellets occupy in the range of about 30% to about 70% of the volume of the insulating sheath.

7. The method as set forth in claim 5
   wherein the insulating sheath has a thickness in the range of about 0.003 inches to about 0.010 inches; and
   wherein each of the pellets has a transverse dimension in the range of about 0.0005 inches to about 0.0010 inches.

8. The method as set forth in claim 5
   wherein the plurality of the pellets occupy in the range of about 30% to about 70% of the volume of the insulating sheath;
   wherein the insulating sheath has a thickness in the range of about 0.003 inches to about 0.010 inches; and
   wherein each of the pellets has a transverse dimension in the range of about 0.0005 inches to about 0.0010 inches.

9. An implantable electrical medical lead extending between proximal and distal ends for use with a pulse generator to be implanted within a human body, the lead comprising:
   at least one electrode;
   a connector configured to provide an electrical connection with the pulse generator;

an electrical conductor within the lead extending between a proximal end attached to the connector and a distal end attached to the at least one electrode; and an insulating sheath normally covering the electrical conductor and extending from the proximal end to the distal end, the insulating sheath having a self-sealing member operative to re-insulate the electrical conductor in the event of an abrasion of the sheath;

wherein the self-sealing member is of polymeric material embedded with a plurality of pellets, each pellet having a frangible shell containing a liquid sealing material that fills the rupture and solidifies when the frangible shell is broken;

wherein the polymeric material of the insulating sheath is selected from the group consisting of silicone or polyurethane or a combination thereof; and wherein the liquid sealing material in each pellet is a body temperature curable adhesive.

* * * * *